(12) United States Patent
Ohmiya et al.

(10) Patent No.: US 7,718,389 B2
(45) Date of Patent: May 18, 2010

(54) STABILIZING COMPOSITION AND STABILIZING METHOD OF COELENTERAZINE SOLUTION FOR HIGH-THROUGHPUT MEASUREMENT OF LUCIFERASE ACTIVITY

(75) Inventors: Yoshihiro Ohmiya, Ikeda (JP); Chun Wu, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 648 days.

(21) Appl. No.: 11/580,500

(22) Filed: Oct. 13, 2006

(65) Prior Publication Data

US 2008/0020384 A1 Jan. 24, 2008

Related U.S. Application Data

(60) Provisional application No. 60/833,105, filed on Jul. 24, 2006.

(51) Int. Cl.
*C12Q 1/66* (2006.01)
(52) U.S. Cl. .......................................... 435/8
(58) Field of Classification Search .................. None
See application file for complete search history.

(56) References Cited

U.S. PATENT DOCUMENTS 5,023,181 A * 6/1991 Inouye ........................ 435/189
6,171,809 B1 * 1/2001 Roelant .......................... 435/8

OTHER PUBLICATIONS

Shimomura et al. Regeneration of the photoprotein aequorin, Nautre, Jul. 17, 1975, vol. 256, pp. 236-238, entire document.*
Johnson FH. et al. Action of cyanide on *Cypridina luciferin*, Journal of Cellular and Comparative Physiology, Jun. 1962, vol. 59, pp. 265-272, entire document.*
Dunstan SL. et al. Cloning and expression of the bioluminescent photoprotein Pholasin from the bivalve mollusc *Pholas dactylus*, The Journal of Biological Chemistry, Mar. 2000, 275(13): 9403-9409, entire document.*
Inouye, S. et al., "The Use of *Renilla* Luciferase, *Oplophorus* Luciferase, and Apoaequorin as Bioluminescent Reporter Protein in the Presence of Coelenterazine Analogues as Substrate," *Biochemical and Biophysical Research Communications*, 233:349-353 (1997).
Wu, Chun et al., "Chemi- and bioluminescence of coelenterazine analogues with a conjugated group at the C-8 position," *Tetrahedron Letters*, 42:2997-3000 (2001).

* cited by examiner

*Primary Examiner*—Jon P Weber
*Assistant Examiner*—Satyendra K Singh
(74) *Attorney, Agent, or Firm*—Wenderoth, Lind & Ponack, L.L.P.

(57) ABSTRACT

The present invention relates to a stabilization composition of coelenterazine or an analog thereof, a kit, a method for measuring a coelenterazine-based biological luminescence, containing coelenterazine or the analog thereof and an antioxidant.

6 Claims, 3 Drawing Sheets

$$\frac{\text{Activity}_{\text{Start}}}{\text{Activity}_{\text{Last}}} > 1$$

STABILIZING COMPOSITION AND STABILIZING METHOD OF COELENTERAZINE SOLUTION FOR HIGH-THROUGHPUT MEASUREMENT OF LUCIFERASE ACTIVITY

This application claims priority to the U.S. Provisional Application No. 60/833,105, filed Jul. 24, 2006. The above-referenced application is hereby expressly incorporated by reference in its entirety.

TECHNICAL FIELD

The present invention relates to a stabilization method for stably measuring an enzyme activity of various luciferases using coelenterazine (*Renilla* luciferin) or an analog thereof as a substrate at room temperature over a long time.

BACKGROUND ART

In the field of life science, the measurement of an activity of gene transcription which occurs in a cell is generally performed, and used for evaluation of effects of foreign factors which affect the cell, analyses of intracellular signal transduction and expression of an individual protein group. In order to quantitatively determine the gene expression in a wide range and analyze temporal dynamic changes of the gene expression, the measurement of gene transcription activity by reporter technology using luciferase which is a luminescent enzyme has been actively performed. Meanwhile, special substances in vivo have been actively evaluated, quantified and analyzed, and in particular, in immunoassays using antibodies, utilizing recognizability of the antibody, from low molecular biomolecules which are specific hormones and physiologically active substances to high molecular proteins have been quantified. At that time, it is common to detect the antibody by a labeling method utilizing radioactivity or chromogenic property, but in recent years, the labeling method using luciferase has been used. Therefore, it becomes a more important theme to improve and develop the luciferase technology for the purpose of elucidating life phenomena.

As major luminescent proteins currently exploited as the luciferase technology, luciferases derived from firefly, *Cypridina*, *Renilla* and copepod, and an aequorin luminescent protein derived from luminescent jellyfish are available. To exploit these luciferases, firefly luciferin, *Cypridina* luciferin, and coelenterazine (other names: *Renilla* luciferin, firefly squid preluciferin, oplophorus luciferin) which is a substrate of *Renilla* luciferase, copepod luciferase and aequorin are available (Table 1). Three luciferins can be directly extracted from luminescent organisms, can also be chemically synthesized and are commercially available.

TABLE 1

Relationship of luciferin and luciferase

| Luciferase | Luciferin |
| --- | --- |
| Firefly luciferase | Firefly luciferin |
| Beetle luciferase | |
| *Cypridina* luciferase | *Cypridina* luciferin |
| *Renilla* luciferase | Coelenterazine (other names: |
| Copepod luciferase | *Renilla* luciferin, firefly squid |
| Oplophorus luciferase | preluciferin, oplophorus |
| Luminescent protein (aequorin) | luciferin) |

Coelenterazine which can be synthesized relatively easily has been already used in many products. For example, a dual assay system supplied from Promega is the system which measures two transcription activities with two substrates by inserting a transcription active region A in a firefly luminescent enzyme gene, simultaneously inserting a transcription active region B in a *Renilla* luciferase gene and introducing two gene constructs in a cell. In this method after lysing the cells, firefly luciferin is added to measure the transcription activity A. The luminescence of firefly luciferase is quenched, and subsequently coelenterazine is added to measure the transcription activity B.

Meanwhile, recently copepod luciferase (*Gaussia* Luciferase U.S. Pat. No. 6,436,682) extracellularly secreted and supplied from Prolume has been noticed. The system in which this gene is introduced into the cell, and taking advantage of synthesized and secreted luciferase, an expression amount of a gene is measured by adding coelenterazine into medium is suitable for the assay with high throughput.

Since a pKa value of proton of an imidazopyrazinone ring in coelenterazine is around 7.4, the proton is easily dissociated in neutral or weak basic buffer. Thus, coelenterazine reacts with oxygen to release faint light with being oxidized and decomposed. In existing methods, it is necessary to store coelenterazine in an alcohol solution under an acidic condition at pH 4 to 5 in a freezer at −20(C or below (Non-patent literature 1). Meanwhile, the optimal pH of the luciferase group using coelenterazine as the substrate is around the neutral, 7 to 8, and is much different from the pH value which stabilizes coelenterazine. In order to reduce the effect of the alcohol solution under the acidic condition, a small amount of luciferin (1/1000, v/v) relative to the luciferase solution is added (Non-patent literature 1).

Since a volume of a well in a 96-well plate or a 384-well plate used in the assay with high throughput is 0.2 mL or less, it is preferable to add 0.2 (L or less of the coelenterazine acidic alcohol solution (Non-patent literature 1). Since the amount of dispensed liquid in an existing luminometer for the 96-well plate is 25 to 250 (L, it is impossible to add the faint amount of the coelenterazine acidic alcohol solution. In addition, in the case of immunoassay, it is desirable to directly add the coelenterazine solution into the washed well. This way, in any cases, it is necessary to dilute coelenterazine with the buffer at pH 7 to 8.

Meanwhile, since coelenterazine is unstable in a weak basic aqueous solution, when coelenterazine is diluted with the buffer at pH 7 to 8, variation of the luciferin activity between the first sample and the last sample appears in the measurement of samples in a large amount. Thus, the correct measurement can not be performed (FIG. 1). Stability of coelenterazine in the buffer at pH 7 to 8 is an important problem for the assay with high throughput. Upon the measurement of coelenterazine, its self-luminescence which is a background is also a factor to reduce a dynamic range, and a reaction solution to reduce the self-luminescence is required.

Non-Patent literature 1: BIOCHEMICAL AND BIOPHYSICAL RESEARCH COMMUNICATIONS 233, 349-353 (1997)

DISCLOSURE OF THE INVENTION

The present invention aims at maximally eliciting a luminescence activity of luciferase using coelenterazine as a substrate and stabilizing coelenterazine or an analog thereof compatible with the analysis with high throughput.

As a result of an extensive study for solving the above problems, the present inventor has established a stabilization technology in which the activity of coelenterazine at room temperature is not reduced and the background can be reduced at around pH 7 to 8 at which the luminescence activity of luciferase using coelenterazine as the substrate is maximized.

The present invention relates to the following inventions.

[1] A stabilization composition of coelenterazine or an analog thereof comprising coelenterazine or the analog thereof and an antioxidant.

[2] A method for storing coelenterazine or an analog thereof characterized in that coelenterazine or the analog thereof is stored in the presence of an antioxidant.

[3] A kit for using for a coelenterazine biological luminescence system, comprising coelenterazine or an analog thereof and an antioxidant.

[4] A method for measuring coelenterazine-based biological luminescence characterized in that biological luminescence is measured in the presence of an antioxidant in a biological luminescence measurement system of coelenterazine-based luciferase and coelenterazine or an analog thereof.

[5] A method for measuring coelenterazine-based biological luminescence characterized in that biological luminescence is measured in the presence of an antioxidant in a biological luminescence measurement system of coelenterazine-based luciferase modified with a physiologically active substance or coelenterazine-based recombinant luciferase and coelenterazine or an analog thereof.

[6] The method according to [5] wherein the physiologically active substance is at least one substance selected from the group consisting of antigens, antibodies, haptens, hormones, enzyme substrates, sugar chains and nucleic acids.

[7] The composition, the method or the kit according to any of [1] to [6] wherein the antioxidant is selected from the group consisting of ascorbic acid or salts thereof, erythorbic acid or salts thereof, and sulfite salts.

In particularly preferable embodiments of the present invention, the method of stabilizing coelenterazine or the coelenterazine analog which maximally elicits the luminescence activity of luciferase using coelenterazine as the substrate and is compatible with the analysis with high throughput is provided. By the use of the stabilization method, the luminescence activity of luciferase using coelenterazine as the substrate can be measured at room temperature with good reproducibility. These can be used for the treatment of pathological states, the examination and drug discovery.

BEST MODES FOR CARRYING OUT THE INVENTION

Figure 1:
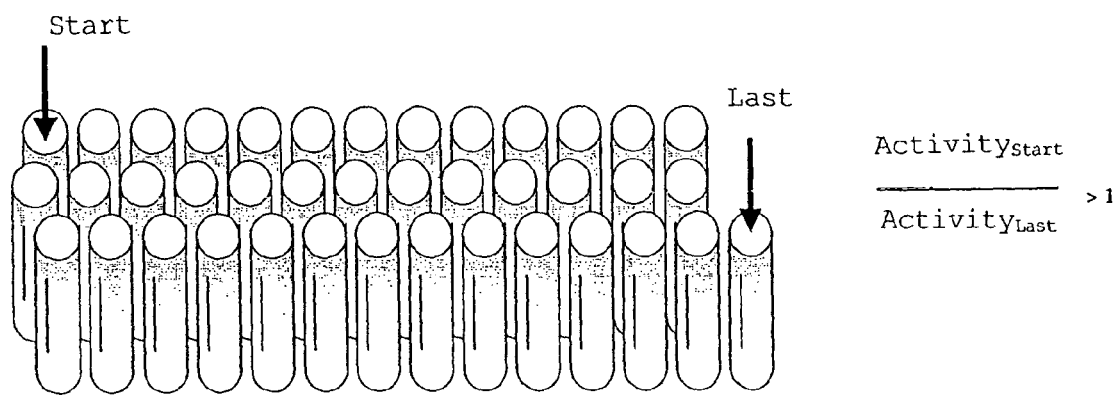
FIG. 1 is an image view showing an assay of coelenterazine with high throughput.

A structure of coelenterazine or an analog thereof is shown below:

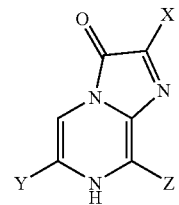

wherein, X represents an aralkyl group which may be substituted, such as 4-hydroxybenzyl, 4-$SO_3H$-benzyl, benzyl and naphthylmethyl groups, or a (cycloalkyl)methyl having 3 to 8 carbon atoms such as cyclohexylmethyl; Y represents an aryl group which may be substituted; Z represents an aralkyl group which may be substituted, a cyclohexylmethyl group, an aryl group which may be substituted, a heterocyclic group which may be substituted, or a —$CH_2$-heterocyclic group which may be substituted.

The aralkyl-group includes benzyl, phenethyl and naphthylmethyl.

The aryl group includes phenyl and naphthyl.

The heterocyclic group includes thienyl, pyrrolyl, imidazolyl, pyrazolyl, thiazolyl, isothiazolyl, pyridyl, pyrazinyl, pyrimidinyl, pyridazinyl, and indolyl.

Substituents for the aralkyl group, the aryl group and the heterocyclic group include alkyl groups such as methyl, ethyl, propyl and butyl having a straight or branched chain and 1 to 6 carbon atoms (may be monosubstituted with hydroxyl or fluorine atom(s) or perfluorinated), halogen atoms (chlorine, fluorine, bromine or iodine), alkanoyl groups such as acetyl having 1 to 6 carbon atoms, alkoxy groups such as methoxy having a straight or branched chain and 1 to 6 carbon atoms, OH, SH, COOH, $SO_3H$, amino groups, amino groups monosubstituted or disubstituted with alkyl group(s) having 1 to 4 carbon atoms such as methylamino and dimethylamino, nitro and cyano, and have 0 to 3, preferably 0, 1 or 2 of these substituents.

Coelenterazine and the analogs thereof are publicly known or can be easily produced by publicly known methods (Non-patent literatures 1 and 2).

Non-patent literatures 2: Tetrahedron Lett., 2001, 42, 2997-3000.

In the present invention, coelenterazine or the analogs thereof can be stabilized by combining coelenterazine or the analogs thereof with an antioxidant. Furthermore, by measuring the biological luminescence system comprising *Renilla* luciferase, copepod luciferase or oplophorus luciferase and coelenterazine or the analog thereof in the presence of the antioxidant, it is possible to augment luminescence signals, reduce the luminescence background and widely improve the S/N ratio.

The antioxidant includes ascorbic acid or salts thereof, erythorbic acid or salts thereof, sulfite salts, butylhydroxyanisole, polyphenols, and hydrogenated boron alkali metals, and these can be used alone or in combination of two or more. Preferably, ascorbic acid and erythorbic acid or the salts thereof are included. When two or more antioxidants are combined, it is preferable to combine ascorbic acid with at least one other antioxidant.

Ascorbate salts, erythorbate salts and sulfite salts include alkali metal salts such as sodium, potassium, lithium and cesium salts, ammonium salts, alkali earth metal salts such as calcium and magnesium salts.

When the antioxidant such as ascorbic acid or salts thereof, erythorbic acid or salts thereof or sulfite salts is added to the biological luminescence system using coelenterazine or the analog thereof, it is preferable to add at a concentration of about 0.005 to 1 M.

The composition comprising coelenterazine or the analog thereof and the antioxidant is suitable for stabilizing coelenterazine or the analog thereof (solution, or solid such as powder, granules and crystals). In the composition, about 40000 to 800000 parts by weight of the antioxidant relative to one part by weight of coelenterazine or the analog thereof is combined.

Therefore, the composition comprising coelenterazine or the analog thereof and the antioxidant (particularly ascorbic acid, erythorbic acid or salts thereof, sulfite salts) is particularly preferable because not only the storage of coelenterazine or the analog thereof is stabilized at room temperature but also the increase of the background upon measurement can be inhibited.

The kit used for the coelenterazine biological luminescence system of the present invention comprises coelenterazine or the analog thereof and the antioxidant, and if necessary further comprises assay buffer and lysis buffer. The assay buffer includes the buffers at pH 6 to 9, preferably pH 7 to 8, and specifically includes Tris buffer, phosphate buffer, acetate buffer, and Good buffer. The lysis buffer includes solutions containing urea, thiourea, DTT, DMSO or CHAPS.

Luminescent proteins by which biological luminescence is measured using coelenterazine or the analog thereof include *Renilla* luciferase, copepod luciferase and oplophorus luciferase.

The stabilization composition/measurement method used in the present invention can be used in the system comprising the above luminescent protein (luciferase) alone, and the luminescent protein may be the protein modified by binding the luminescent protein to the physiologically active substance to form a complex. By the use of such a complex, the amount of the physiologically active substance can be quantified. The physiologically active substance is not particularly limited, and includes, for example, antigens, antibodies, haptens, hormones, enzyme substrates, sugar chains and nucleic acids (DNA, RNA).

EXAMPLES

The present invention will be described in more detail below according to Examples, but it goes without saying that the present invention is not limited thereto.

Example 1

Figure 2:
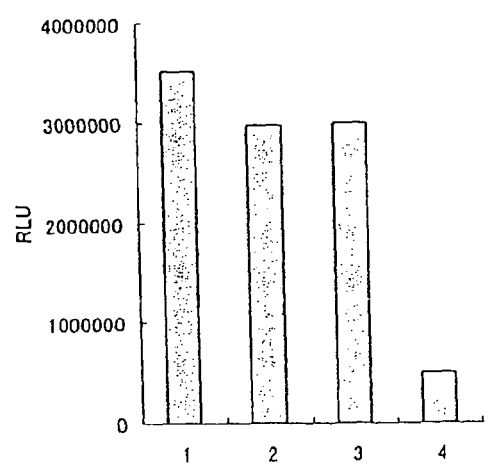
FIG. 2 is a graph showing a luminescence activity of coelenterazine in the presence of a stabilizer.
Figure 3:
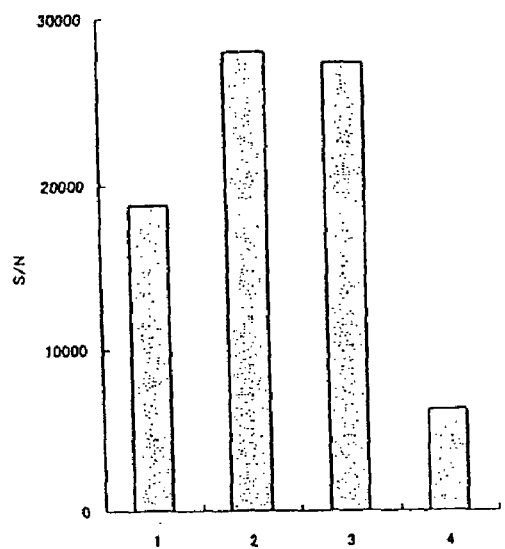
FIG. 3 is a graph showing a luminescence S/N ratio of coelenterazine in the presence of a stabilizer.
Figure 4:
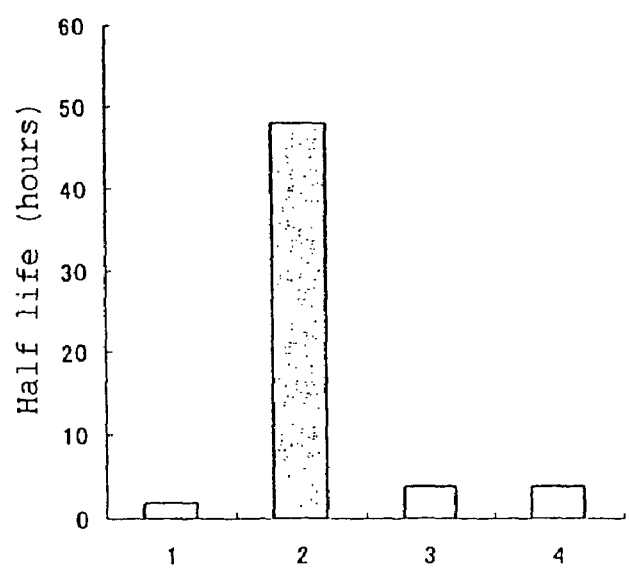
FIG. 4 is a graph showing a half life of coelenterazine in the presence of a stabilizer.

Luminescence Activity and S/N Value of Coelenterazine in the Presence of Stabilizer The following four types of solutions (1, 2, 3, 4) were prepared, coelenterazine was dissolved at a final concentration of 0.001 mM, and a background activity was measured. Subsequently, *Renilla* luciferase was added, the luminescence activity (RLU: relative light unit) was measured, and actual measurement values are shown in FIG. 2. The S/N value obtained by dividing RLU by the background value initially measured is shown in FIG. 3. As a result, it was found that the sodium ascorbate salt solution 2 and the sodium sulfite salt solution 3 gave the low background and good S/N.

In FIGS. 2, 3 and 4,
  1: 0.1 M Tris-HCl pH 7.4/0.3 M NaCl
  2: 0.1 M Tris-HCl pH 7.4/0.3 M Sodium ascorbate
  3: 0.1 M Tris-HCl pH 7.4/0.2 M $Na_2SO_3$
  4: 0.1 M Tris-HCl pH 7.4/0.2 M Thiourea Using *Renilla* luciferase, the residual activity of coelenterazine in the above solutions 1, 2, 3 and 4 was examined to determine the half life of coelenterazine in each solution. As a result, 10 times longer prolongation of the half life was observed in the sodium ascorbate salt solution than in the other solutions. From the above results, it was found that the sodium ascorbate salt solution was the best in the luminescence activity measurement with high throughput using coelenterazine.

Example 2

Self-Luminescence Activity of Coelenterazine in 10% FBS Solution

Figure 5:
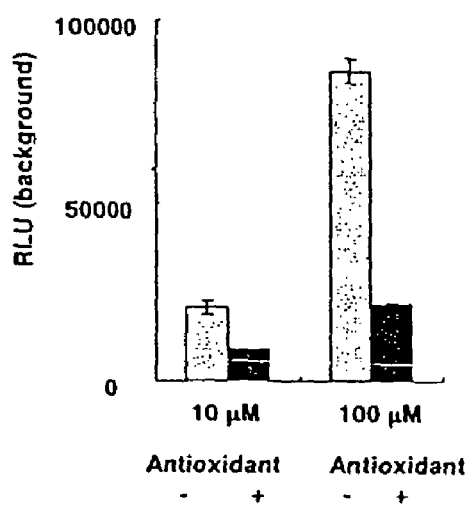
FIG. 5 is a graph showing a self-luminescence activity of coelenterazine in a 10% FBS solution.

The following two types of the solutions (1) and (2) were prepared, coelenterazine was dissolved at a final concentration of 10 μM or 100 μM, the resulting solution was mixed with the medium (containing 10% FBS) for animal cells at 1:1 (volume ratio), and the luminescence for 10 seconds was measured as the background activity. The results are shown in FIG. 5.

(1) 0.1 M Tris-HCl pH 7.4/0.3 M NaCl (2) 0.1 M Tris-HCl pH 7.4/0.3 M Sodium ascorbate Example 3

Ratio of Luminescence to Self-Luminescence by Copepod Luciferase

Figure 6:
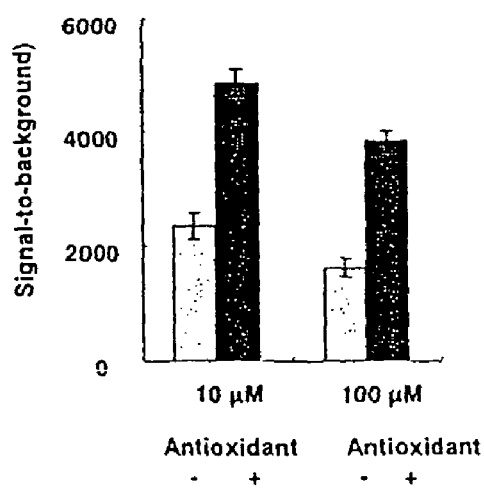
FIG. 6 is a graph showing a ratio of luminescence to self-luminescence by copepod luciferase.

The medium (containing 10% FBS) in which copepod luciferase had been secreted from animal cells was reacted with the coelenterazine solution (final concentration of 10 μM or 100 μm) prepared in Example 2, the luminescence activity (RLU) was measured, and the ratio of the actual measured value to the self-luminescence was calculated and summarized in FIG. 6. As a result, the ratio of the luminescence to the self-luminescence was improved at least two times or more in the sodium ascorbate salt solution.

INDUSTRIAL APPLICABILITY

The present invention can be practically applied to the followings.

1) Dual assay system with high throughput by *Cypridina* (including *Vargula*) luciferase and copepod luciferase genes: The transcription active region A is inserted in a *Cypridina* luminescent enzyme gene, simultaneously the transcription active region B is inserted in a copepod luciferase gene, and two gene constructs are introduced in a cell. After passing over a certain time period, portions of the medium are removed, and a half thereof is dispensed in one of two 96-well plates. A *Cypridina* luciferin solution is added to one plate to assay the transcription activity A. A coelenterazine stabilization solution is added to the other plate to assay the transcription activity B. One transcription activity is normalized by making the transcription active region A or B a control gene sequence (e.g., SV40, CMV promoter). Although it takes a long time to measure the luminescence activity of all samples in the 96-well plate, by the use of the coelenterazine stabilization solution, it is possible to measure the luminescence values with high reproducibility.

2) Immunoassay with high throughput by copepod luciferase: Since copepod luciferase is stable at room temperature for a long time, the immunoassay is performed by making a biotin-labeled copepod luciferase/streptoavidin complex, detecting a subject substance by the antibody using a sandwich method or a competitive inhibition method and using the biotin-labeled copepod luciferase/streptoavidin complex as a secondary antibody. Although it takes a long time to measure the luminescence activity of all samples, by the use of the coelenterazine stabilization solution, it is possible to measure the luminescence values with high reproducibility.

The invention claimed is:

1. A stabilization composition of coelenterazine or an analog thereof comprising—coelenterazine or its analog of formula (I)

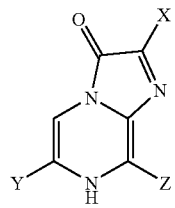

(I)

wherein, X represents an aralkyl group which may be substituted and is selected from the group consisting of 4-hydroxybenzyl, 4-SO$_3$H-benzyl, benzyl and naphthylmethyl groups, or a (cycloalkyl)methyl having 3 to 8 carbon atoms; Y represents an aryl group which may be substituted; Z represents an aralkyl group which may be substituted, a cyclohexylethyl group, an aryl group which may be substituted, a heterocyclic group which may be substituted, or a —CH$_2$-heterocyclic group which may be substituted, and an antioxidant selected from the group consisting of ascorbic acid, erythorbic acid and salts thereof,
wherein the stabilized composition is suitable for use in a *Gaussia* luciferase assay.

2. A method for storing coelenterazine or an analog thereof comprising storing the stabilization composition of claim 1.

3. A kit for a coelenterazine biological luminescence system, comprising a composition comprising coelenterazine or its analog of formula (I)

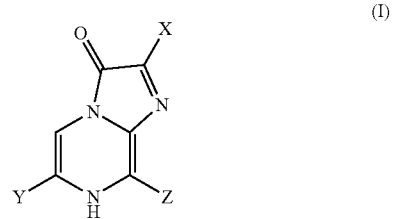

(I)

wherein, X represents an aralkyl group which may be substituted and is selected from the group consisting of 4-hydroxybenzyl, 4-SO$_3$H-benzyl, benzyl and naphthylmethyl groups, or a (cycloalkyl)methyl having 3 to 8 carbon atoms; Y represents an aryl group which may be substituted; Z represents an aralkyl group which may be substituted, a cyclohexylethyl group, an aryl group which may be substituted, a heterocyclic group which may be substituted, or a —CH$_2$-heterocyclic group which may be substituted, and an antioxidant selected from the group consisting of ascorbic acid, erythorbic acid and salts thereof,
wherein the stabilized composition is suitable for use in a *Gaussia* luciferase assay.

4. A method for measuring *Gaussia* biological luminescence comprising contacting the stabilization composition of claim 1 with *Gaussia* luciferase and measuring *Gaussia* biological luminescence.

5. A method for measuring *Gaussia* biological luminescence comprising contacting the stabilization composition of claim 1 with *Gaussia* luciferase modified with a physiologically active substance or *Gaussia* recombinant luciferase, and measuring *Gaussia* biological luminescence.

6. The method according to claim 5 wherein the physiologically active substance is at least one substance selected from the group consisting of antigens, antibodies, haptens, hormones, enzyme substrates, sugar chains and nucleic acids.

* * * * *